(12) United States Patent
Isolauri et al.

(10) Patent No.: US 7,172,756 B2
(45) Date of Patent: Feb. 6, 2007

(54) METHODS OF PROMOTING TOLEROGENIC IMMUNE RESPONSES AND COMPOSITIONS THEREFOR

(75) Inventors: Erika Isolauri, Raisio (FI); Leena Metsäniitty, Helsinki (FI); Hannu Korhonen, Riihimäki (FI); Seppo Salminen, Turku (FI); Eeva-Liisa Syvaoja, Espoo (FI)

(73) Assignee: Valio Oy, Helsinki (FI)

( * ) Notice: Subject to any disclaimer, the term of this patent is extended or adjusted under 35 U.S.C. 154(b) by 359 days.

(21) Appl. No.: 10/321,661

(22) Filed: Dec. 18, 2002

(65) Prior Publication Data

US 2003/0113340 A1 Jun. 19, 2003

Related U.S. Application Data

(63) Continuation of application No. 08/973,963, filed as application No. PCT/FI96/00350 on Jun. 12, 1996, now Pat. No. 6,506,380.

(30) Foreign Application Priority Data

Jun. 14, 1995 (FI) .................................... 952926

(51) Int. Cl.
  A01N 63/00 (2006.01)
  A23J 1/00 (2006.01)
  A23J 1/02 (2006.01)
  C12N 1/20 (2006.01)
(52) U.S. Cl. .................. 424/93.45; 426/656; 426/657; 435/252.1; 514/2
(58) Field of Classification Search ............. 424/93.45; 426/656, 657; 435/252.1; 514/2
See application file for complete search history.

(56) References Cited

U.S. PATENT DOCUMENTS

| | | | | |
|---|---|---|---|---|
| 3,886,288 | A * | 5/1975 | Rice et al. | |
| 4,839,281 | A * | 6/1989 | Gorbach et al. | ............... 435/34 |
| 5,112,812 | A | 5/1992 | Samuelsson et al. | |
| 5,578,302 | A * | 11/1996 | Brassart et al. | |
| 5,952,034 | A * | 9/1999 | Buchanan et al. | |
| 6,506,380 | B1 * | 1/2003 | Isolauri et al. | ........... 424/93.45 |

FOREIGN PATENT DOCUMENTS

| | | |
|---|---|---|
| DE | 281540 | 8/1990 |
| EP | 0199535 | 10/1986 |
| EP | 0322589 | 7/1989 |
| EP | 0601802 | 6/1994 |
| EP | 0629350 | 12/1994 |
| EP | 0683984 | 11/1995 |
| JP | 52079083 * | 7/1977 |
| JP | 75156666 | 7/1977 |
| JP | 520790863 | 7/1977 |
| JP | 548785 | 1/1979 |
| JP | 93339097 | 1/1995 |
| JP | 93339097 | 6/1995 |

OTHER PUBLICATIONS

Isolauri et al, Gastroenterology 105:1643-1650, 1993.*
Khalid et al (J. Dairy Sci. vol. 73 pp. 3068-3076), 1990.*
Bjorksten (Current Opinion in Allergy and Clinical Immunology vol. 5, No. 3, pp. 249-253, Jun. 2005).*
Wróblewska et al., "The Effect of Selected Microorganisms on the Presence of Immunoreactive Fractions in Cow and Goat Milks", *Polish Journal of Food and Nutrition Sciences*, 1995, vol. 4/45, No. 3, pp. 21-29.
Journal of Nutrition Research and Food Science—Prof. Dr. W. Heeschen, vol. 50, pp. 241-300, 1995, with English translation of paragraph 5 on p. 246.
Wroeblewska, et al., "The Effect of Selected Microorganisma on the Presence of Immunoreactive Fractions in Cow and Goat Milk" Polish Journal of Food and Nutrition Sciences, 1995, vol. 4/45, No. 3, pp. 21-29.
Polish Journal of Food and Nutrition Sciences—Pol. J. Food Nurt. Sci., vol. 4/45, No. 3, 1995.
Isolauri, et al., Gastroenterology, vol. 105, pp. 1643-1650, 1993.
Robert Hansen—North European Food and Dairy Journal—Should Acidophilus-Bifido Products be Produced from Hydrolyzed Milk?—1989, No. 8-9, pp. 203-204.
Erika Isolauri, et al., Pediatrics, A Human Lactobacillus Strain (*Lactobacillus casei* sp Strain GG) Promotes Rocovery form Acute Diarrhea In Children, 1991, pp. 90-97, vol. 88, No. 1.
Simo Siitonen, et al., Annals of Medicine, Effect of Lactobacillus GG Yoghurt in Prevention of Antibiotic Associated Diarrhoea, 1990, pp. 57-59, vol. 22.
Minna Kaila, et al, Pediatric Research, Enhancement of the circulating Antibody Secrecting Cell Response in Human Diarrhea by a Human *Lactobacillus* Strain, 1992, pp. 141-144, vol. 32, No. 2.
E. Isolauri, et al., "*Lactobacillus casei* strain GG reverses increased intestinal permeability induced by cow milk in suckling rats" Department of Clinical Medicine, University of Tampere, Finland, Gastroenterology, Dec. 1993, vol. 105, No. 6, pp. 1643-1650 (Abstract Only).
Khalid, et al., J. Dairy Science, vol. 73, pp. 3068-3076, 1990.
Aggett et al., "Comment on antigen-reduced infant formulae," *Acta Paediatr.*, 1993, pp. 314-319, vol. 82.

* cited by examiner

*Primary Examiner*—Mark Navarro
(74) *Attorney, Agent, or Firm*—Nelson Mullins Riley & Scarborough

(57) ABSTRACT

Methods and compositions for promoting tolerogenic immune responses or treating immune responses to food antigens comprise *Lactobacillus* GG. Oral administration of *Lactobacillus* GG to patients such as human infants may promote a tolerogenic immune response to antigens in cow's milk.

4 Claims, 5 Drawing Sheets

METHODS OF PROMOTING TOLEROGENIC IMMUNE RESPONSES AND COMPOSITIONS THEREFOR

CROSS-REFERENCE TO RELATED APPLICATIONS

This application is a continuation of application Ser. No. 08/973,963, filed May 29, 1998, now U.S. Pat. No. 6,506,380, as the National Stage of International Application No. PCT/FI96/00350, filed Jun. 12, 1996, and claims the priority of Finnish Patent Application No. 952926, filed Jun. 14, 1995.

FIELD OF THE INVENTION

The present invention relates to methods and means of suppressing food-induced hypersensitivity reactions in patients suffering from food allergy. Particularly the invention provides methods of preventing or treating allergies, especially cow's milk allergy in infants. The invention also relates to development of specific formulae for allergic infants with impaired gut barrier function.

BACKGROUND OF THE INVENTION

Cow's milk allergy (CMA) is defined as an immune-mediated adverse reaction to cow's milk proteins. The present treatment of choice is the complete elimination of cow's milk antigens. In infants with CMA, it is necessary to use a substitute formula when human milk is unavailable. Hydrolysed formulae, based on cow's milk-derived whey or casein, are used to provide adequate nutrition with a reduced antigenic load. The preliminary heat treatment of cow's milk mainly affects the conformation of proteins and facilitates their hydrolysis. Subsequent enzymatic hydrolysis with pepsin, trypsin, pancreatic extracts and extracts from the intestinal mucosa causes progressive destruction of sequential epitopes and refines the formulae into the least antigenic and allergenic form.

In most cases, extensively hydrolysed cow's milk-derived formulae can be safely introduced and these are efficient and clinically and metabolically well tolerated. Enzymatic hydrolysis, however, does not necessarily make the formulae nonallergenic, as the optimal extent of hydrolysis is not known and traces of the original protein are detected in the hydrolysate. Therefore, introduction of these substitutes to children with cow's milk allergy must be cautious.

The approach to control allergic inflammation by antigen elimination has not been satisfactory, particularly in patients with multiple food allergies (Sampson et al., 1992). These patients frequently show increased intestinal permeability and dysfunction of the intestine's defence barrier (Majamaa et al., 1996, Majamaa and Isolauri, 1996). This enhances the risk for growth disorders and sensitization to multiple foods. New approaches are urgently needed for the treatment of cow's milk allergy to improve the substitute formulae in CMA.

Intestinal antigen handling determines subsequent immune response to the antigen. In health, antigens are absorbed across epithelium along two functional pathways. The main pathway is degradative reducing the immunogenicity of the antigen. A minor pathway allows the transport of intact proteins which is crucial for antigen-specific immune responses. Aberrant antigen absorption enhances the sensitization process (Fargeas et al., 1995).

Differential production of cytokines by T-helper (Th) cells during an immune reaction has important regulatory effects on the nature of the immune response. The cytokine profile of the natural immune response determines the phenotype of the subsequent specific immune response. Apart from controlling IgE synthesis, IL-4 is crucial for the development and maturation of the Th2 phenotype, characterized for allergic inflammation.

This process appears crucial for the development of tolerance to ingested protein. Oral tolerance is a state of antigen-specific systemic non-responsiveness characterized by local antigen-specific IgA response.

An isolated human intestinal strain, *Lactobacillus* strain GG (*Lactobacillus* GG, ATCC 53103) has recently been shown to promote local IgA responses against dietary antigens encountered by the enteric route and may therefore aid in immune elimination (Isolauri et al., 1993). It is not as yet known whether particular strains of intestinal bacteria could directly modify the immunogenicity of the food antigens and consequently downregulate hypersensitivity reactions.

Lactobacilli are included in the microbial flora of healthy intestines. It has been assumed that Lactobacilli act in the intestinal tract by competing for receptors and nutrients against pathogenic microbes on the intestinal mucosa.

Probiotics are viable microbial preparations which promote health by maintaining the natural microflora in the gut. A microbial preparation can be acknowledged as a probiotic if the functioning microbes thereof and their mode of action are known. The probiotics attach on the intestinal mucosa, colonize the human intestinal tract and prevent attachment of harmful microbes. A crucial presumption is that they get up to the gut's mucosa and do not get destroyed in the upper part of the gastrointestinal tract. *Lactobacillus* GG is one of known bacteria having probiotic characteristics.

SUMMARY OF THE INVENTION

The present inventors have now found that certain bacteria of the gastrointestinal tract, especially Lactobacilli, and especially bacteria having probiotic characteristics, can be used to enhance the efficacy of elimination diets and to improve the oral tolerance, in preventing or treating food-induced hypersensitivity reactions in a patient.

One aspect of the invention is that protein hydrolysates obtained by hydrolysis of proteins with above mentioned gastrointestinal bacteria can also be used to said purpose. We show here that protein hydrolysates obtained according to this invention have an immunological effect promoting hypoallergenicity. The hydrolysates downregulate hypersensitivity reactions thus promoting the gut immune barrier function, i.e., stabilising the gut musocal barrier.

The present invention provides an improved protein hydrolysate formula downregulating hypersensitivity reactions and promoting the gut immune barrier function. The hydrolysate formula is obtainable by hydrolysing proteins with enzymes obtained from probiotic gastrointestinal bacteria, especially Lactobacilli, which have adhesive and colonizing characteristics and a protease enzyme system which are similar to those of the strain *Lactobacillus* GG (ATCC 53103), and with trypsin and/or pepsin.

Alternatively, a protein hydrolysate formula of the invention can be obtained by hydrolysing proteins with trypsin and/or pepsin, and adding to the hydrolysate so obtained a bacterial preparation comprising probiotic gastrointestinal bacteria, especially Lactobacilli, which have adhesive and colonizing characteristics and a protease enzyme system which are similar to those of the strain *Lactobacillus* GG (ATCC 53103). The bacteria are added into the hydrolysate formula preferably as a lyophilized preparation.

While administering such a hydrolysate formula to a patient, it is to be expected that the hydrolysing enzymes of the bacteria present are released in vivo whereby the same effect is achieved as with an improved hydrolysate formula as defined above. In addition, the viable bacteria stabilize the gut mucosal barrier enhancing the local defence.

An embodiment of this invention is a method of preventing or treating food-induced hypersensitivity reactions in an infant, which method comprises the step of administering to an infant at risk the improved protein hydrolysate formula of the invention, or alternatively a protein hydrolysate formula together with a bacterial preparation comprising probiotic gastrointestinal bacteria, especially Lactobacilli, which have adhesive and colonizing characteristics and a protease enzyme system which are similar to those of the strain Lactobacillus GG (ATCC 53103).

A further embodiment of this invention is a method of treating cow's milk allergy in a patient, comprising administering to the patient the improved protein hydrolysate formula of the invention or, alternatively administering a protein hydrolysate formula together with a bacterial preparation comprising probiotic gastrointestinal bacteria, especially Lactobacilli, which have adhesive and colonizing characteristics and a protease enzyme system which are similar to those of the strain Lactobacillus GG (ATCC 53103).

The invention also provides a method of promoting tolerogenic immune responses to food antigens in a patient, comprising oral administration of the improved protein hydrolysate formula of the invention to the patient, or, alternatively, a bacterial preparation comprising probiotic gastrointestinal bacteria, especially Lactobacilli, which have adhesive and colonizing characteristics and a protease enzyme system which are similar to those of the strain Lactobacillus GG (ATCC 53103), or, alternatively, a protein hydrolysate formula together with a bacterial preparation comprising probiotic gastrointestinal bacteria, especially Lactobacilli, which have adhesive and colonizing characteristics and a protease enzyme system which are similar to those of the strain Lactobacillus GG (ATCC 53103).

In the methods of the invention as defined above, when a protein hydrolysate formula is used in combination with selected probiotic bacteria as defined above, such a formula can be any suitable protein hydrolysate formula, known or novel. It can thus be either a partial protein hydrolysate, or alternatively an extensively hydrolysed formula. Preparation of a protein hydrolysate suitable for this purpose is disclosed e.g. in EP patent application No. 601 802.

Preferred bacterium to be used in the formulae and methods of the invention is Lactobacillus GG (ATCC 53103).

In this specification and in the appended claims the phrase "bacteria, especially Lactobacilli, which have adhesive and colonizing characteristics and a protease enzyme system which are similar to those of the strain Lactobacillus GG (ATCC 53103)" should be understood to define bacteria whose adhesive and colonizing characteristics are comparable to those of the LGG strain, e.g. as defined in EP-patent 199 535. These bacteria are also supposed to have same kind of enzyme system as LGG, which means that enzymes derived from such bacteria are able to degrade proteins to produce hydrolysation products with same effects as those obtained using enzymes derived from LGG.

| | Abbreviations |
|---|---|
| CI | Confidence interval |
| IFN-γ | Interferon-γ |
| IgA | Immunoglobulin A |
| IgE | Immunoglobulin E |
| IL-4 | Interleukin-4 |
| LGG | Lactobacillus GG (ATCC 53103) |
| OKT3 | anti-CD3 antibody |
| PBMC | peripheral blood mononuclear cells |
| TNF-α | tumor necrosis factor α |
| WF | test group receiving extensively hydrolysed Whey Formula |
| WF-GG | test group receiving extensively hydrolysed Whey Formula and LGG preparation |
| P/T-casein = | casein hydrolysed by pepsin and trypsin |
| P/T-$\alpha_{s1}$-casein = | $\alpha_{s1}$-casein hydrolysed by pepsin and trypsin |

BRIEF DESCRIPTION OF THE DRAWINGS

FIGS. 1A–1D Mitogen-induced proliferative responses of PBMCs in vitro to P/T-casein (1A), P/T-$\alpha_{s1}$-casein (1B), P/T-casein additionally hydrolysed with LGG derived enzymes (1C) and P/T-$\alpha_{s1}$-casein additionally hydrolysed with LGG derived enzymes (1D). Results are expressed as mean counts per minute for cultures without hydrolysed product (PHA-RPMI 1640) and with hydrolysed product at three concentrations (0.1, 10 and 1000 μg/ml). Horizontal lines represent the geometric mean of counts per minute of the six experiments, enumerated the same for each individual.

Figure 1A:
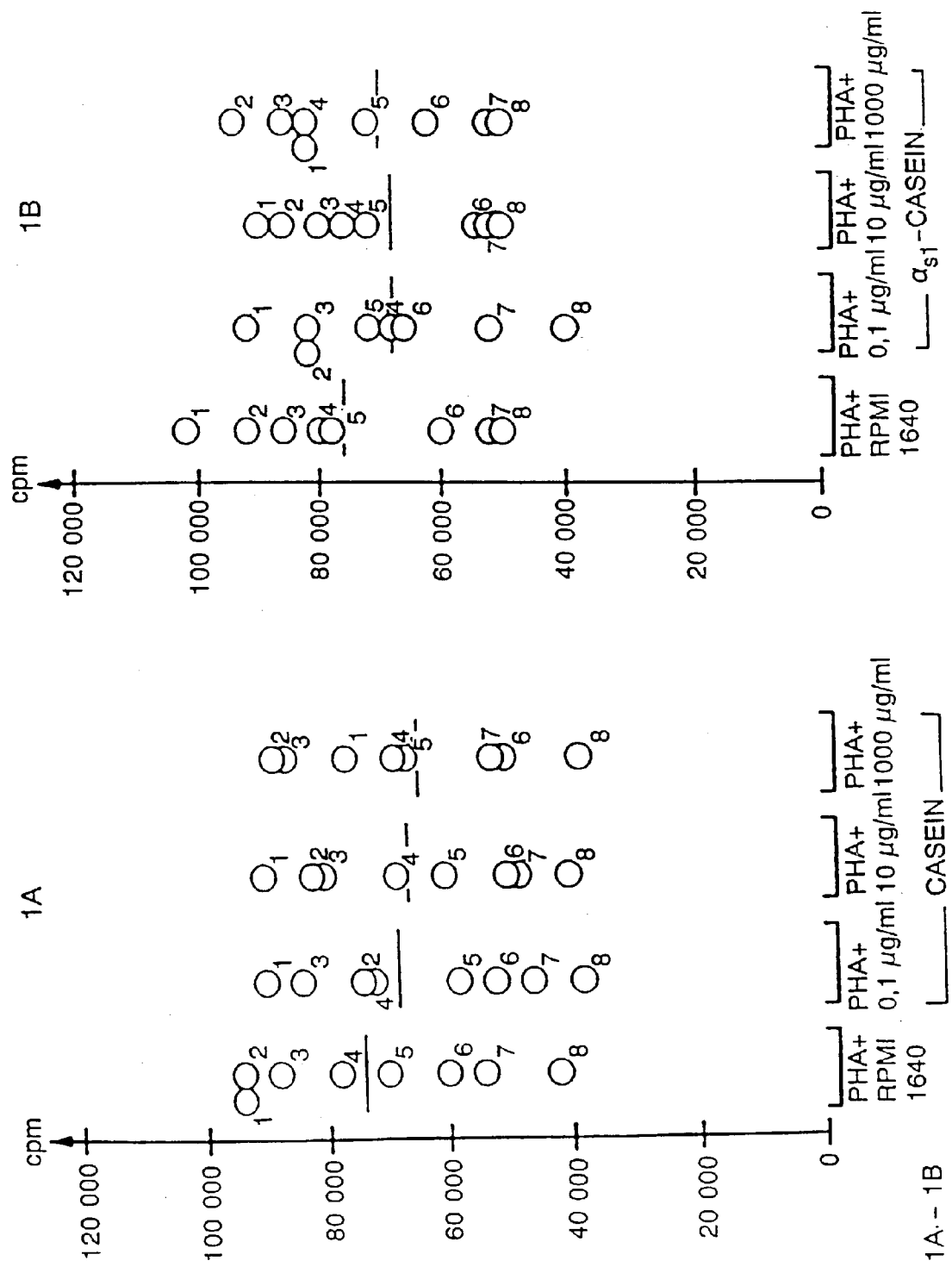

The following examples illustrate the invention further. Methods for preparing the improved hydrolysate are described, as well as experiments showing the beneficial therapeutic effect observed in the present studies.

DETAILED DESCRIPTION OF THE INVENTION

EXAMPLE 1

Suppression of Lymphocyte Proliferation In Vitro by Bovine Caseins Hydrolysed with *Lactobacillus* GG Derived Enzymes 1.a. Hydrolysis of Cow's Milk Proteins Bovine total casein and casein components ($\alpha_{s1}$-casein) were purified from cow milk (Syväoja, 1992). The hydrolysis with the enzyme mixture obtained from *Lactobacillus* GG was applied separately to casein and $\alpha_{s1}$-casein. The enzymes were isolated using the modified method of Exterkate and de Veer, 1985. Briefly, the enzymes were released by sonication of frozen bacterial cells. The supernatant of the centrifuged cells was separated and used for the hydrolysis of casein and $\alpha_{s1}$-casein. The hydrolysis was carried out for 24 h at 34° C.

The GG-hydrolysate so obtained were further hydrolysed with pepsin and trypsin. Briefly, the samples were hydrolysed first with 0.1% pepsin in 0.1 mol/1 HCl for 3 hours at 37° C., pH 2.5. After pH adjustment with 250 mg NaHCO$_3$ and 2 mol/1 NaOH, 0.1% trypsin was added to the samples and these were hydrolysed for 5 hours at 37° C., pH 8.0.

P/T-casein and P/T-$\alpha_{s1}$-casein samples were obtained by hydrolysing the purified casein and $\alpha_{s1}$-casein only with pepsin and trypsin as described above, without GG-hydrolysation.

1.b Lymphocyte Transformation Test

A modification of the whole blood micromethod for mitogen-induced lymphocyte transformation was used. Six to eight healthy individuals volunteered as blood donors for the experiment. Briefly, heparinized venous blood was obtained and diluted 1:7 with RPMI 1640 culture medium (Grand Island Biological Co. NY, USA) containing antibiotics. Phytohemagglutinin (PHA) (Difco Laboratories, Detroit, Mich., USA) was diluted with RPMI 1640 containing antibiotics, with ranges of final concentrations in cultures from 5 to 1250 µg/ml. Lyophilized hydrolysates of casein and $\alpha_{s1}$-casein were diluted in RPMI 1640 to their final concentrations of 0.1 µg/ml (low), 10 µg/ml (medium) and 1000 µg/ml (high) as proven to be nontoxic on T cells in dye exclusion studies with eosin.

Two sets of experiments were undertaken to investigate the mitogen-induced proliferative responses of peripheral blood monoclear cells (PBMCs) to (A) casein hydrolysed with pepsin and trypsin (=P/T-casein), (B) $\alpha_{s1}$-casein hydrolysed with pepsin and trypsin (=P/T-$\alpha_{s1}$-casein), (C) P/T-casein additionally hydrolysed with *Lactobacillus* GG derived enzymes, and (D) P/T-$\alpha_{s1}$-casein additionally hydrolysed with *Lactobacillus* GG derived enzymes.

Experiment consisted of four control cultures with different dilutions of the culture medium and the mitogen, as well as corresponding test cultures with 25 µl of hydrolysed products at three different concentrations. The assay was carried out as described in Sütas et al., 1996.

The mitogen-induced proliferation of PBMCs was expressed as counts per minute, background excluded. The results were presented for control cultures containing 125 µg/ml PHA and RPMI 1640 and for the three test cultures containing 125 µg/ml PHA and hydrolysed products at the low, medium, and high concentrations.

1.c. Statistical Analysis

A nonparametric pairwise test (Wilcoxon signed-rank test) was used to compare the change of the values in counts per minute of each of the test cultures with those of the control cultures. The level of significance was p<0.05. Significant results of pairwise comparisons were presented as suppression or stimulation according to decrease or increase of the values in counts per minute in the test culture.

1.d. Results

Figures 1C, 1D:
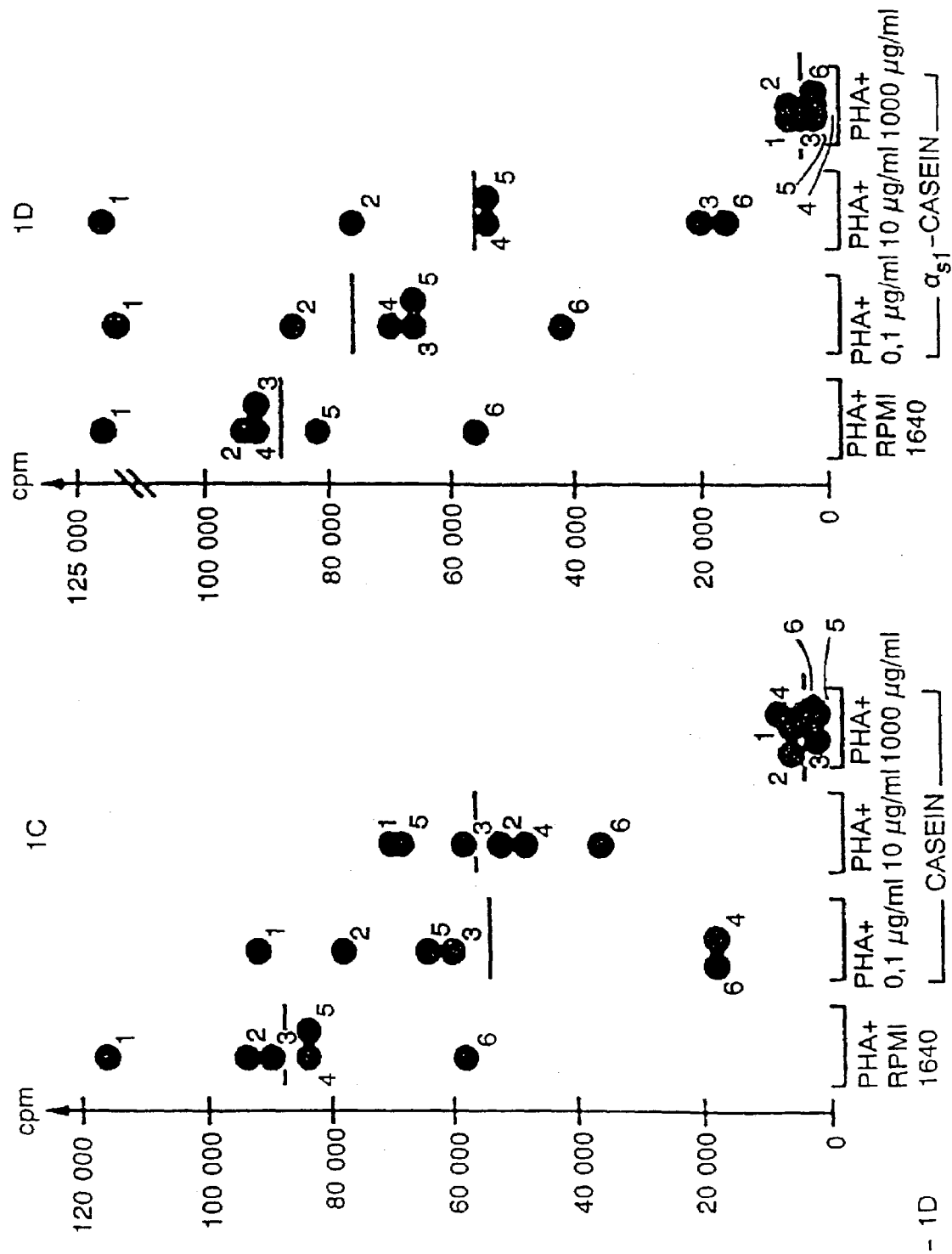

In the experiments done with P/T-casein and P/T-$\alpha_{s1}$-casein additionally hydrolysed with *Lactobacillus* GG derived enzymes, the mitogen included proliferation of PBMCs was significantly suppressed at 0.1, 10 and 1000 µg/ml (p=0.03, p=0.03, and p=0.03) (FIGS. 1C and 1D) compared to P/T-casein and P/T-$\alpha_{s1}$-casein (FIGS. 1A and 1B).

EXAMPLE 2

The treatment of Infants with Atopic Dermatitis with Protein Hydrolysate Formula Supplemented with Lactic Acid Bacteria 2.a. Patients and Study Design The study comprised 31 infants, aged 2.5 to 15.7 (mean age 8) months, fulfilling the Hanifin criteria (Hanifin 1987) for atopic eczema in children. They had been referred to a paediatric clinic on the basis of atopic eczema and suspected cow's milk allergy. The mean age at onset of symptoms was 2.4 months. Duration of total breast-feeding was 5.9 months. A positive family history of atopic diseases (asthma, atopic eczema and allergic rhinitis) or food allergy in first-degree relatives was noted in 26 (84%) patients. The eczematous lesions were treated with emollients and topical corticosteroids. No patient was receiving systemic corticosteriod therapy. Besides atopic eczema, gastrointestinal disturbances such as loose stools, vomiting or diarrhea were seen in 9 (19%) patients. After the study periods the patients were allocated to double-blind placebo-controlled cow's milk challenge. Only those having a positive reaction (27/31) were included in the final study population.

The patients were randomized to two groups for one month. One group (WF, n=14) received extensively hydrolysed whey formula (Valio Ltd, Helsinki, Finland, EP-A-601802) and another group (WF-GG, n=13) received the same formula with additional *Lactobacillus* GG preparation ($5\times10^8$ cfu/g) (supplied by Valio Ltd, Helsinki, Finland). After the one-month therapy with their assigned formulae; both groups received an extensively hydrolysed whey formula (Valio Ltd) for one additional month. The serum total IgE concentration, cow's milk-specific IgE (RAST, Pharmacia, Uppsala, Sweden) and skin prick tests were determined from all patients before dietary intervention. Prick testing was done on the volar aspect of the forearm, using a commercially available cow milk allergen ALK (Allergologisk Laboratorium, Horsholm, Denmark) and test formula diluted to normal feed concentration. A 1 mm single-peak lancet with shoulder to prevent deeper penetration (ALK) was used, with histamine dihydrochloride 10 mg per milliliter (ALK) as positive control. Reactions were read after 15 minutes, and a response half of the histamine reaction size or more was recorded as positive on condition that the mean diameter of the wheal was at least 3 mm and the negative control at the same time 0 mm.

Faecal samples for the determination of α-1 antitrypsin and TNF-α were collected before the commencement of the management and 1 (corresponding to the study period) and 2 months later.

The severity of atopic dermatitis was scored according to the SCORAD method, established by the European Task Force on Atopic Dermatitis (1993). Briefly, the extent (score A) of the dermatitis was estimated using the rule of nines. The intensity (score B) of the dermatitis was the sum of the individual scores (0–3) for erythema, oedema and/or papules, excoriation, lichenfication and dryness. The subjective (score C) manifestations (Scored 1–10), including pruritus and sleep loss, were assessed from parents' estimations. SCORAD was obtained with the calculation: A/5+3.5×B+C.

The study protocol was approved by the Ethical Review Committee of Tampere University Hospital. An informed consent was obtained from the parents.

2.b. Determination of α-1 Antitrypsin in Faecal Specimens

Frozen faecal specimens were thawed at room temperature and homogenized. Approximately 1 g was transferred to a glass tube and lyophilized. The resulting dry material was ground and 50 mg transferred to an Eppendorf tube. One ml of 0.15 M NaCl solution was added, and α-1 antitrypsin was extracted by vigorous mixing in a Vortex mixer for 20 minutes at room temperature. The resulting suspension was centrifuged at 25,000 g for 10 minutes to remove the debris, and the supernatant was used for the determination of α-1 antitrypsin using a Behring BNA nephelometer according to the manufacturer's instructions. The results are given as mg/g dry weight for lyophilized faeces.

2.c. Determination of TNF-α in Faecal Specimens

Deep-frozen faecal specimens were thawed at room temperature, suspended 1:1 (w/v) in physiological saline and allowed to sediment. Of the supernatant, 0.5–1.0 ml was transferred to an Eppendorf tube and centrifuged at 25,000 g for 10 minutes. The supernatant was then used for the determination of TNF-α. A commercial enzyme immunoassay (Human TNF-α ELISA Kit, Endogen Inc., Boston, Mass., USA) was used, as instructed for serum specimens, for the determinations of faecal TNF-α.

2.d. Statistics

By reason of the skewed distributions of serum IgE concentrations, logarithmic (ln) transformation was used and data are presented as means with 95% confidence intervals (CI). The concentrations of inflammatory parameters are presented with medians with lower and upper quartiles. The Wilcoxon signed rank test and the Mann-Whitney U-test were used in statistical comparisons.

2.e. Results 2.e.1. Clinical Data

The mean (95% CI) serum total IgE was 31 (15–61) kU/l in patients receiving the hydrolysate formula. RAST for cow's milk was positive (>0.4 kU/1) in 10/31 (37%) atopic eczema patients. Skin prick test for cow's milk was positive in 8/31 (30%) patients.

Figure 2:
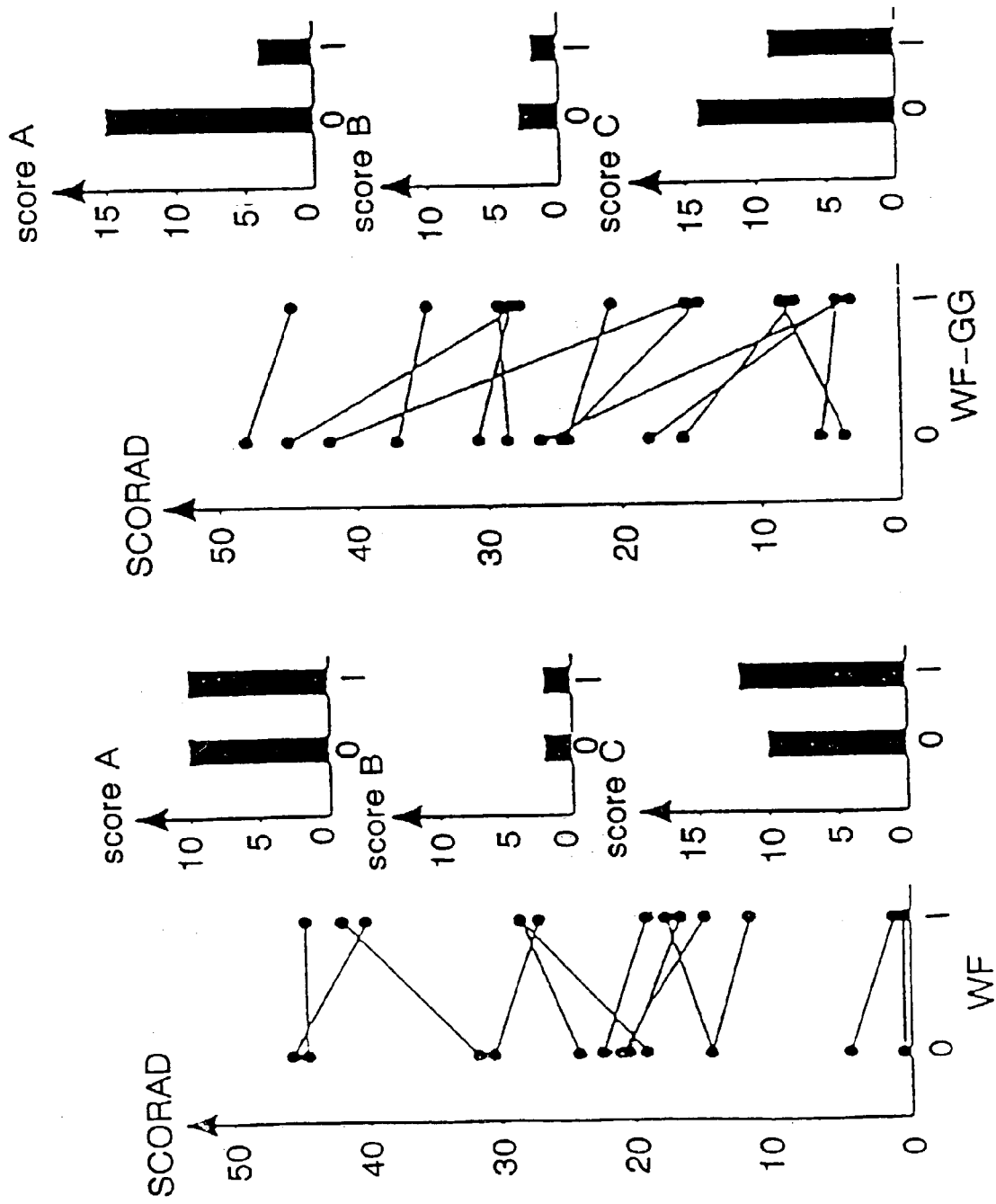
FIG. 2 The clinical score of atopic dermatitis (SCORAD) in each patient and the median score for extent (A), intensity (B) and subjective score (C) for atopic dermatitis before management (0) and one month later (I) in infants receiving extensively hydrolysed whey formula without (WF) or the same with Lactobacillus GG (WF-GG).

The severity of atopic dermatitis in each patient before the commencement of the managements and one month later, i.e. after the study period are presented in FIG. 2. The median (lower quartile-upper quartile) SCORAD score was 21(14–31) in group WF and 26 (17–38) in group WF-GG before management (p=0.33). There was a significant improvement of SCORAD score after one month's intervention in those receiving Lactobacillus GG (p=0.008), but not in those receiving extensively hydrolysed formula without Lacbobacillus GG (p=0.89). The SCORAD score was then 19 (13–31) in group WF and 15 (7–28) in group WF-GG. The decrease in the SCORAD score in WF-GG was due to the reduction of the extent (score A, p=0.004), intensity (score B, p=0.05) and subjective score (score C, p=0.01) for atopic dermatitis (FIG. 2). The improvement of SCORAD score was achieved by 2 months in the WF group, and in group WF-GG in remained unchanged after cessation of Lactobacillus GG. At 2 months, the median (lower quartile-upper quartile) SCORAD score in group WF was 14(2–38) and in group WF-GG 16(6–25).

2.e.2. The concentrations of α-1 antitrypsin and TNF-α in faeces

In healthy controls (n=9), the median (lower quartile-upper quartile) concentration of α-1 antitrypsin was 0.5 (0.5–1.7) mg/g. The concentration of α-1 antitrypsin was comparable between groups WF and WF-GG before management (p=0.22). As indicated in Table 1, the concentration of α-1 antitrypsin decreased significantly in group WF-GG (p=0.03), but not in group WF (p=0.68) during the one month study period. At two months, the concentration of α-1 antitrypsin was 1.2 (0.5–1.6) in WF and 0.5 (0.5–0.7) in WF-GG.

The concentration of faecal TNF-α was 0 (0–0.08) pg/g in healthy controls. The concentration of faecal TNF-α was significantly higher in atopic children, p<0.0001 (Table 1). The concentration of TNF-α was comparable between the groups WF and WF-GG before management (p=0.57). The concentration of faecal TNF-α decreased significantly in WF-GG (p=0.003) but not in WF (p=0.38) during the one month study period (Table 1). A reduction in TNF-α concentration was achieved by 2 months in group WF, while in group WF-GG who were also given the extensively hydrolysed formula without Lactobacillus GG a tend to increased TNF-α was detected. The concentration of TNF-α was then 84 (25–129) in WF and 144 (20–338) in WF-GG.

TABLE 1

The concentrations of faecal α-1 antitrypsin and TNF-α before management (0) and one month later (I) in infants receiving extensively hydrolysed whey formula (WF) or the same formula containing Lactobacillus GG bacteria (WF-GG). Data denote median (lower quartile–upper quartile).

|  | WF | WF-GG |
| --- | --- | --- |
| α-1 antitrypsin 0 (mg/g) | 1.7 (1.5–2.3) | 1.4 (0.5–1.9) |
| α-1 antitrypsin I (mg/g) | 1.7 (1.1–2.8) | 0.5 (0.5–1.0) |
| TNF-α 0 (pg/g) | 632 (126–1880) | 709 (91–1131) |
| TNF-α I (pg/g) | 494 (147–1009) | 34 (19–103) |

EXAMPLE 3

Downregulation of Cytokine Production by Peripheral Blood Mononuclear Cells in Atopic Children 3.a Patients and Methods Altogether, 14 patients aged 5–29 (mean, 16) months who fulfilled the Hanifin criteria for atopic dermatitis (Hanifin, 1987) and eight age-matched non-atopic healthy children were studied. None were receiving systemic corticosteroids at the time of the study.

OKT3 (anti-CD3-antibody) containing ascites fluid was a kind gift from Dr M. Kaartinen, Department of Bacteriology and Immunology, University of Helsinki, Helsinki, Finland.

Bovine total casein had been purified from bovine milk as described in Syväoja (1992). Purified casein was hydrolysed with *Lactobacillus* GG-derived enzymes as described in Example 1. Purified casein or *Lactobacillus* GG-degraded casein were lyophilized and stored at room temperature. Before experiments, they were diluted in RPMI 1640 and filter sterilization (0.1 μm, Millipore Corporation, Bedford, Mass., USA) was applied.

Complete culture medium consisted of RPMI 1640 with 10% foetal calf serum, 10 mM Hepes buffer, 2 mM L-glutamin (Gibco Life Technologies, Paisley, UK), 50 U/ml benzyl-penicillin (Sigma, St. Louis, Mo., USA), 10 mg/ml gentamycin (Roussel Laboratories Ltd, Uxbridge, Middlesex, UK). Peripheral venous blood (5 ml) was obtained. PBMC containing 90% lymphoid cells was isolated by FicollPaque (Pharmacia Biotech, Uppsala, Sweden) gradient centrifugation and suspended at $1 \times 10^6$ cells/ml in compete culture medium. Culture wells were precoated with anti-CD3 antibody containing ascites fluid at a pretested optimal dilution. The test culture additionally contained dilution of casein or *Lactobacillus* GG-degraded casein at a final concentration of 1 mg/ml. These experiments were repeated for purified bovine $\alpha_{s1}$-casein or Lactobacillus GG-degraded $a_{s1}$-casein. After 24 h of incubation in a humidified 5% $CO_2$ atmosphere at 37° C., supernatants were collected and stored at −70° C. for cytokine assays. IL-4 and IFN-γ in culture supernatants were determined by commercially available ELISA kits according to manufacturers' instructions (IL-4: CLB, Compact Human Interleukin-4 ELISA kit, Central Laboratory of The Netherlands Red Cross Blood Transfusion Service, Amsterdam, The Netherlands; IFN-γ. EIFNG, Endogen Inc., Cambridge, Mass., USA). The results from different runs were equalized employing the comparison of standard curves and were expressed as pg/ml. The sensitivity of the assays for IL-4 was 2.3 pg/ml and for IFN-γ, 5 pg/ml. Wilcoxon signed-rank test was used in statistical comparisons of the test cultures to the control cultures. The level of significance was $P<0.05$.

3.b. Results

Figure 3:
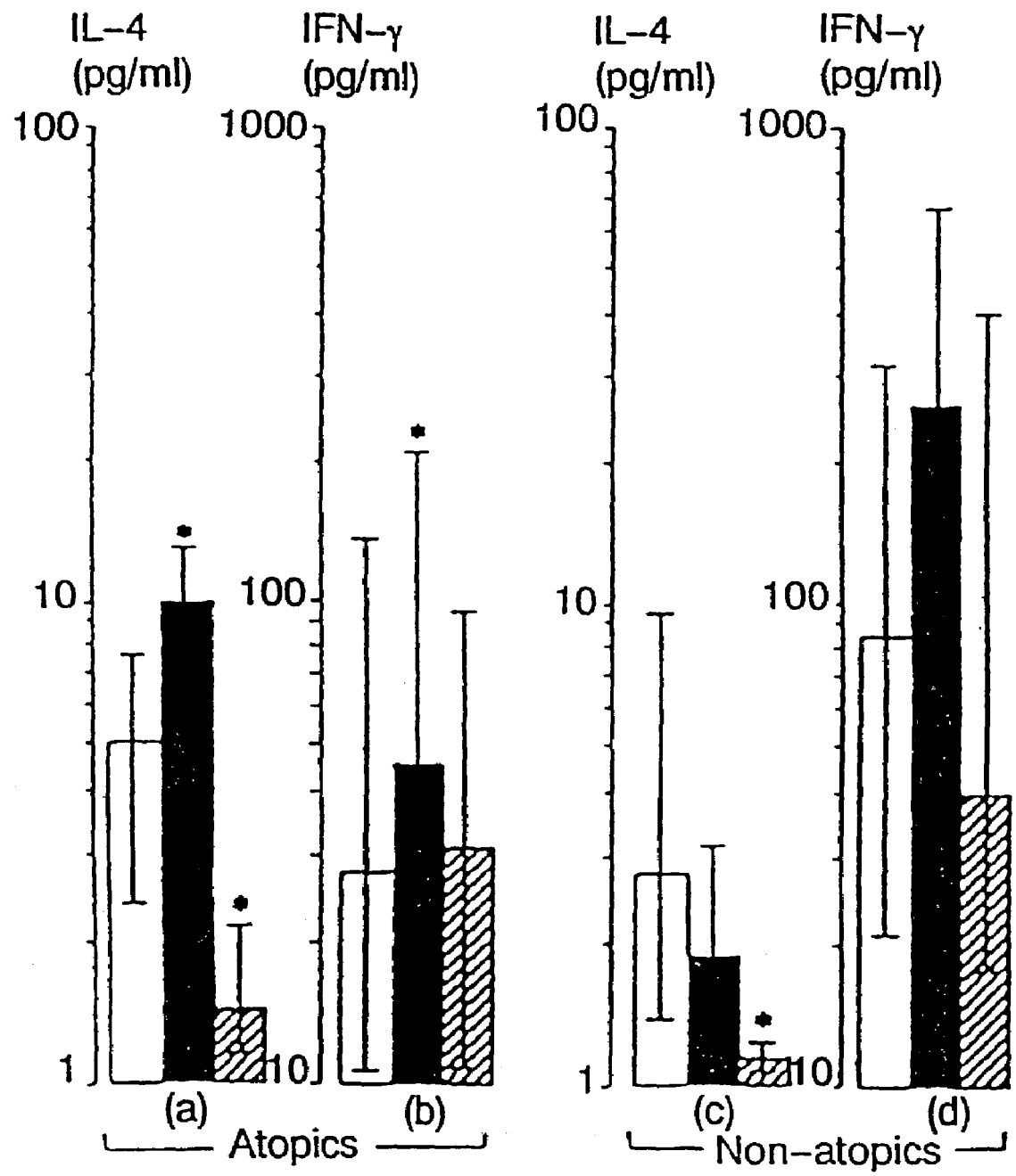
FIG. 3 The effect of casein and Lactobacillus GG-degraded casein on the production of IL-4 and IFN-γ by PBMC in atopic patients (a, b) and in nonatopic healthy children (c,d). White columns represent the median cytokine production in control cultures; black columns, in cultures containing purified casein; and hatched columns, in cultures containing Lactobacillus GG-degraded casein. Intersecting lines represent the upper and lower quartiles. *Statistically significant pairwise comparison to control cultures.

In atopic patients, both IL-4 and IFN-γ production were increased in cultures containing purified casein when compared to control cultures, $P=0.008$ and $P=0.008$, respectively (FIG. 3a,b). No such effect of bovine casein was observed when degraded by enzymes of *Lactobacillus* GG. Conversely, the IL-4 production in cultures containing *Lactobacillus* GG-degraded casein was significantly less than in control cultures, $P=0.003$ (FIG. 3a), and the IFN-γ production in these cultures was comparable to control cultures, $P=0.10$ (FIG. 3b).

Figure 4:
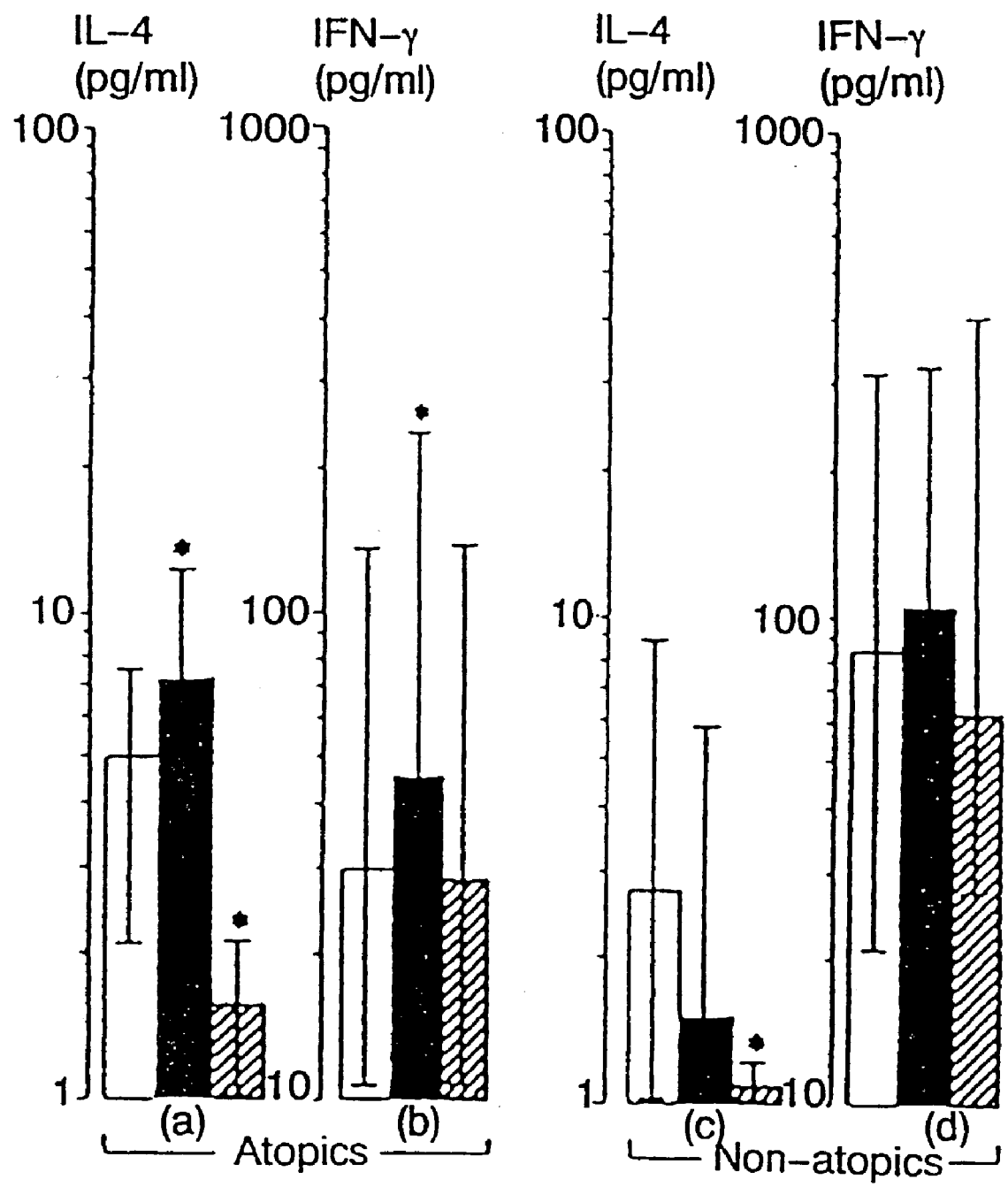
FIG. 4 The effect of $\alpha_{s1}$-casein and Lactobacillus GG-degraded $\alpha_{s1}$-casein on the production of IL-4 and IFN-γ by PBMC in atopic patients (a,b) and in nonatopic healthy children (c,d). White columns represent the median cytokine production in control cultures; black columns, in cultures containing $\alpha_{s1}$-casein; and hatched columns, in cultures containing Lactobacillus GG-degraded $\alpha_{s1}$-casein. Intersecting lines represent the upper and lower quartiles. *Statistically significant pairwise comparison to control cultures.

In healthy children, the production of IL-4 and IFN-γ in cultures containing purified casein were comparable to control cultures, $P=0.10$ and $P=0.10$ (FIG. 3c,d). In parallel to the findings in atopic patients, healthy children had significantly less IL-4 production in cultures containing *Lactobacillus* GG-degraded casein than in control cultures, $P=0.01$ (FIG. 3c) and the IFN-γ production in these cultures remained comparable to control cultures, $P=0.50$ (FIG. 3d). Parallel results were obtained with $\alpha_{s1}$-casein and *Lactobacillus* GG-degraded $\alpha_{s1}$-casein (FIG. 4).

REFERENCES

European task force on atopic dermatitis. Severity scoring of atopic dermatitis: the SCORAD index. Dermatology 1993; 186:23–31.

Exterkate F and de Veer G. Partial isolation and degradation of caseins by cell wall proteinase(s) of *Streptococcus cremoris*. Appl Environ Microbiol 1985; 49:328–32.

Fargeas M J, Theodorou V. More J. Wal J M, Fioramonti, Bueno L. Boosted systemic immune and local responsiveness after intestinal inflammation in orally sensitized guinea pigs. Gastroenterology 1995; 109:53–62.

Hanifin J M. Epidemiology of atopic dermatitis. Monogr Allergy 1987; 21:116–131.

Isolauri E, Majamaa H, Arvola T, Rantala I, Virtanen E, Arvilommi H. *Lactobacillus casei* strain GG reverses increased intestinal permeability induced by cow milk in suckling rats. Gastroenterology 1993; 105:1643–1650.

Majamaa H, Isolauri E. Evaluation of gut mucosal barrier: evidence for increased antigen transfer in children with atopic eczema. J Allergy Clin Immunol 1996, in press.

Majamaa H, Miettinen A, Laine S, Isolauri E. Intestinal inflammation in children with atopic eczema: faecal eosinophil cationic protein and tumor necrosis factor-α as non-invasive indicators of food allergy. Clin Exp. Allergy 1996; 26:181–187.

Sampson H A, James M J and Bernhisel-Broadbent J. Safety of an amino acid-derived infant formula in children allergic to cow milk. Pediatrics 1992; 90:463–465.

Sütas Y, Soppi E, Korhonen H, Syväoja E L, Saxelin M, Rokka T, Isolauri E. Suppression of lymphocyte proliferation in vitro by bovine caseins hydrolyzed with *Lactobacillus casei* GG derived enzymes. J Allergy Clin Immunol 1996, in press.

Syväoja E L. Quantitative determination of the main casein components and purification of $\alpha_{s2}$- and κ-casein from bovine milk. Milchwissenschaft 1992; 47:563–566.

The invention claimed is:

1. A method of promoting tolerogenic immune responses to food antigens in a patient who either has a positive family history of allergy or exhibits food allergic reactions himself, comprising orally administering a bacterial preparation comprising *Lactobacillus* GG (ATCC 53103) to the patient.

2. A method according to claim 1, wherein the food antigens are antigens in cow's milk.

3. A method according to claim 1, wherein the patient is a human.

4. A method according to claim 3, wherein the patient is an infant.

* * * * *